(12) United States Patent
Li (10) Patent No.: US 12,391,582 B2
(45) Date of Patent: Aug. 19, 2025

(54) WATER NEGATIVE ION GENERATING DEVICE AND CONTROL CIRCUIT ARRANGEMENT THEREOF

(71) Applicant: Ya Li, Taizhou (CN)

(72) Inventor: Ya Li, Taizhou (CN)

(73) Assignee: Zhejiang Shuilitchi Health Technology Co., Ltd, Taizhou (CN)

( * ) Notice: Subject to any disclaimer, the term of this patent is extended or adjusted under 35 U.S.C. 154(b) by 0 days.

(21) Appl. No.: 18/726,824

(22) PCT Filed: Dec. 25, 2023

(86) PCT No.: PCT/CN2023/141562
§ 371 (c)(1),
(2) Date: Jul. 5, 2024

(87) PCT Pub. No.: WO2024/187896
PCT Pub. Date: Sep. 19, 2024

(65) Prior Publication Data
US 2024/0417286 A1 Dec. 19, 2024

(30) Foreign Application Priority Data
Mar. 15, 2023 (CN) .......................... 202310244905.2

(51) Int. Cl.
*C02F 1/46* (2023.01)
*A61L 9/14* (2006.01)
(Continued)

(52) U.S. Cl.
CPC ............ *C02F 1/4608* (2013.01); *A61L 9/145* (2013.01); *B01D 47/066* (2013.01);
(Continued)

(58) Field of Classification Search
CPC .... C02F 1/4608; C02F 1/008; C02F 2201/46; F24F 8/30; F24F 8/194; F24F 6/12; F24F 8/192; F24F 8/80; F24F 2120/10; A61L 9/145; A61L 2209/132; A61L 2209/16; A61L 2209/213; A61L 9/14; A61L 9/12; A61L 9/03; A61L 2209/12; A61L 9/22; A61L 2209/135; A61L 2209/14; A61L 2209/134; A61L 2209/111; B01D 47/066; B01D 46/46; B01D 46/0032;
(Continued)

(56) References Cited

U.S. PATENT DOCUMENTS

2011/0162528 A1* 7/2011 Yamaguchi ............ A45D 19/16
261/78.2
2016/0031708 A1* 2/2016 Machi ....................... A61L 9/12
422/186.2

FOREIGN PATENT DOCUMENTS

| CN | 108613264 | 10/2018 |
|---|---|---|
| CN | 110048309 | 7/2019 |
| CN | 216790465 | 6/2022 |

* cited by examiner

*Primary Examiner* — Xiuyu Tai
(74) *Attorney, Agent, or Firm* — Ying-Ting Chen (57) ABSTRACT

A control circuit arrangement for a water negative ion generating device includes a water mist generating circuit for driving the generation of negative ion water mist, and a high voltage charging circuit for supplementing electrons to the negative ion water mist generated by the water mist generating circuit, wherein the water mist generating circuit and the high voltage charging circuit are grounded together, thereby ensuring that the two circuits work normally and produce negative ions.

2 Claims, 8 Drawing Sheets

(51) Int. Cl.
  *B01D 47/06* (2006.01)
  *B05B 17/06* (2006.01)
  *C02F 1/00* (2023.01)
  *F24F 8/30* (2021.01)

(52) U.S. Cl.
  CPC .......... *B05B 17/0607* (2013.01); *C02F 1/008* (2013.01); *F24F 8/30* (2021.01); *A61L 2209/132* (2013.01); *A61L 2209/16* (2013.01); *A61L 2209/213* (2013.01); *C02F 2201/46* (2013.01)

(58) Field of Classification Search
  CPC .............. B01D 46/442; B01D 46/4263; B01D 46/0028; B01D 46/0047; B01D 2273/30; B01D 2279/65; B05B 17/0607; B05B 3/0427; B05B 17/0692; B05B 7/0075; B05B 5/053; B05B 5/057; B05B 5/0533; B05B 5/0255; Y02A 50/20; F21V 33/0064; B03C 3/41; B03C 3/38; B03C 3/04; B03C 3/155; B03C 3/368; B03C 3/011; B03C 3/68; B03C 2201/06; B03C 2201/24; H01T 23/00; C01B 13/11; C01B 2201/22

See application file for complete search history.

WATER NEGATIVE ION GENERATING DEVICE AND CONTROL CIRCUIT ARRANGEMENT THEREOF

CROSS REFERENCE OF RELATED APPLICATION

This is a U.S. National Stage under 35 U.S.C. 371 of the International Application Number PCT/CN2023/141562, filed Dec. 25, 2023, which claims priority under 35 U.S.C. 119(a-d) to Chinese application number 202310244905.2, filed Mar. 15, 2023, wherein the above patent applications are hereby incorporated by reference in their entities.

BACKGROUND OF THE PRESENT INVENTION

Field of Invention

The present invention relates to the field of negative ion technology, and particularly to a water negative ion generating device and control circuit arrangement thereof.

Description of Related Arts

Negative ions have the function of air purification, such as dust removal, sterilization. A conventional negative ion generating machines generally use high-voltage ionization of the air to form negative ions. In order to obtain a higher concentration of negative ions, a relatively high voltage is required. However, extremely high voltage can generate static electricity and ozone. In addition, when the negative ion generating equipment generates negative ions, it is easy to cause charge accumulation, which may cause breakdown of the equipment and affect the safe use of the equipment.

By vibrating and impacting water, negative ions are generated and the negative ions are supplemented with electrons through an ionization assembly, so that a higher concentration of negative ions can be obtained. In this way, the ionization assembly does not require a particularly high voltage, and the generated negative ions tend to be saturated and have strong binding force. Even when the migration distance is long, the negative ions can still remain intact.

However, the negative ion generating equipment has different circuits. It is necessary to design the circuit and protect the components in the circuit in order to ensure the normal operation of the negative ion generating equipment to generate negative ions, and prevent short circuits in the circuit, so that it can be used safely.

SUMMARY OF THE PRESENT INVENTION

To solve the above technical problems, the present invention provides a control circuit arrangement for a water negative ion generating device, comprising:
  a water mist generating circuit for driving the generation of negative ion water mist; and
  a high voltage charging circuit for supplementing electrons to the negative ion water mist generated by the water mist generating circuit, wherein the water mist generating circuit and the high voltage charging circuit are grounded together.

Preferably, the water mist generating circuit comprises a sprayer element and a water negative ion spraying control unit electrically connected to the sprayer element, and the high voltage charging circuit comprises an ionization needle and an ionization control unit electrically connected to the ionization needle.

Preferably, the water negative ion spraying control unit of the water mist generating circuit comprises a boost transformer T1, a power inductor L1, and a protective component DR3 which are electrically connected, wherein the protective component DR3 is connected in parallel with the sprayer element.

Preferably, the protective component DR3 is a bidirectional suppression transient diode with a reverse breakdown voltage not exceeding a maximum excitation voltage of the sprayer element.

Preferably, the sprayer element comprises an spraying piece with spraying holes and a piezoelectric ceramic piece.

Preferably, the ionization control unit comprises a DC to high voltage drive module which increases a voltage to −2 KV or above (such as −2 KV, −3 KV, −4 KV, −5 KV, etc.), wherein the ionization needle is electrically connected to the DC to high voltage drive module to generate negative ions, wherein the high voltage charging circuit further comprises an antistatic assembly which is used to eliminate static electrons generated by the ionization needle and attached to the water negative ion generating device, wherein the antistatic assembly comprises one or more DK2, and a sum of the DC reverse voltage withstand of the DK2 is greater than a high voltage generated by the DC to high voltage drive module.

Preferably, the antistatic assembly also comprises one or more DR2 connected in series with DK2, wherein DR2 can be a transient diode, a varistor, an air discharge tube, a glass discharge tube, a semiconductor discharge tube, or a combination thereof.

Preferably, the antistatic assembly comprises an antistatic connection line, and one or more DKs which are connected in series in the antistatic connection line.

Preferably, at least a part of the antistatic connection line is attached to a housing of the water negative ion generating device.

Preferably, the antistatic assembly further comprises a DC power supply terminal protection assembly connected to the DC to high voltage drive module, wherein the DC power supply terminal protection assembly comprises a diode M1 with a DC reverse voltage withstand of not less than 1 KV to prevent interference from the high voltage charging circuit affecting the system power supply VCC.

Preferably, the ionization control unit comprises a first electrical connection line electrically connected to GND and a second electrical connection line electrically connected to VCC. The DC power supply terminal protection assembly further comprises at least one DR1, wherein one end of DR1 is electrically connected to the second electrical connection line, and the other end is electrically connected to GND, wherein DR1 is a transient diode.

Preferably, the DC power supply terminal protection assembly further comprises at least one PLM1, wherein one end of PLM1 is electrically connected to the second electrical connection line, and the other end is electrically connected to GND, wherein PLM1 is one or more of a transient diode, a varistor, an air discharge tube, a glass discharge tube, and a semiconductor discharge tube.

Preferably, the DC to high voltage drive module increases the voltage to −4 KV~−12 KV.

The present invention also provides a water negative ion generating device, comprising:
  a water storage container having a water storage chamber;
  a water negative ion spraying structure for vibrating and rubbing the water from the water storage container; and
  the above mentioned control circuit arrangement, wherein the water mist generating circuit is used to drive the water negative ion spraying structure to generate the negative ion water mist, and the high voltage charging circuit is used to supplement electrons to the negative ion water mist generated by driving the water mist generating circuit with the water negative ion spraying structure, wherein the water mist generating circuit and the high voltage charging circuit are grounded together.

Preferably, the water negative ion spraying structure comprises:
  a holder element with a placement channel;
  a friction buffer element which is arranged in the placement channel and has water absorption and elasticity;
  a prayer element which is used to vibrate and rub the water in the friction buffer element;
  an insulation layer having a through hole, wherein the prayer element is located between the insulation layer and the holder element; and
  an electrical conductive layer arranged on an outer surface of the holder element and the insulation layer, wherein the electrical conductive layer has a discharge channel, the discharge channel of the electrical conductive layer corresponds to the position of the through hole of the insulation layer to allow the charged water droplets generated by the sprayer element to be released through the through hole of the insulation layer and the discharge channel of the electrical conductive layer to the outside of the water negative ion spraying structure.

Preferably, the sprayer element comprises an spraying piece and a ring-shaped piezoelectric ceramic piece stacked on the spraying piece. The spraying piece has spraying holes. When a predetermined frequency and peak voltage are applied to the spraying piece and the piezoelectric ceramic piece, the spraying piece will vibrate and strike the water droplets in the friction buffer element, thereby generating tiny water droplets through water resonance. At the same time, the tiny water droplets rub against the spraying piece for further acquiring negative electrons and forming negative ions which then diffuse into the environment through the spraying holes.

Preferably, the spraying piece is made of a material that is easier to lose electrons than water, or the surface of the spraying piece is coated with a coating, and the coating is polyimide, aluminum, or polyamide.

Preferably, an aperture size of the spraying holes of the spraying piece is less than 10 micrometers.

Preferably, the holder element has a connecting channel, and the connecting channel forms the placement channel and a guiding channel, and the guiding channel communicates with the water storage chamber of the water storage container, thereby guiding the water in the water storage chamber of the water storage container to the friction buffer element in the placement channel.

Preferably, the connecting channel of the holder element further has a buffering channel, the buffering channel is located between the guiding channel and the placement channel, and the buffering channel and the placement channel are arranged in the horizontal direction, and the guiding channel is arranged in the vertical direction, and the friction buffer element is only located in the placement channel and is prevented from entering the buffering channel.

The present invention also provides a water negative ion air conditioner which comprises an air conditioning main body and the above-mentioned water negative ion generating device. The advantageous effects of the present invention are:
(1) By grounding the water mist generating circuit and the high voltage charging circuit together, so that the two circuits form a closed loop of electron flow, thereby ensuring that the two circuits work normally and produce negative ions.
(2) The water negative ion spraying structure is used to vibrate the water at high frequency, thereby generating small water droplets. At the same time as the generation of small droplets, the spraying piece rubs against and has frictional contact with the small water droplets to simulate the way a waterfall hits the ground and naturally generates a high concentration of beneficial negative ions for human health.
(3) The high voltage charging circuit is used to supply the negative ions generated by the water negative ion spraying structure with additional charges, so that the two can work together to produce a high concentration of negative ions.
(4) High concentration negative ion water mist containing $O_2$-negative molecular group $O_2$—$(H_2O)_n$, H+ negative water molecular group $H_3O_2$—$(H_2O)_n$, HO-negative water molecular group $OH$—$(H_2O)n$, and negative water molecule —$(H_2O)n$ can be generated during the process of the high frequency vibration and rub of water.
(5) The DR3 of the water mist generating circuit is a bidirectional suppression transient diode which can prevent the high voltage generated by the high voltage charging circuit from entering the sprayer element through the housing of the negative ion generating device, so as to control the voltage within a safe range and provide protection.
(6) The high voltage charging circuit provides antistatic function through the antistatic component and protects the power supply through the DC power supply terminal protection assembly, thus ensuring the safe and sustainable operation of the high voltage charging circuit.

In the figures: 1000—water negative ion air conditioner, 1001—air conditioning main body, 100—water negative ion generating device, 200—water mist generating circuit, 300—high voltage charging circuit;
- 10—water negative ion spraying structure, 11—holder element, 111—connecting channel, 112—groove, 1111—guiding channel, 1112—buffering channel, 1113—placement channel, 12—sprayer element, 121—spraying piece, 122—piezoelectric ceramic piece, 1211—spraying hole, 13—friction buffering element, 14—insulation layer, 141—through hole, 15—electrical conductive layer, 151—discharge channel, 152—opening, 20—water storage container, 21—water storage chamber;
- 30—control circuit board, 31—water negative ion spraying control unit, 32—ionization control unit, 321—DC to high voltage drive module, 322—antistatic assembly, 3221—antistatic connection line, 3222—electrical conductive attaching layer, 323—DC power supply terminal protection assembly, 324—first electrical connection line, 325—second electrical connection line, 33—power module;
- 40—fan element, 41—fan, 42—air filter layer;
- 50—ionization assembly, 51—ionization needle, 52—needle frame.

DETAILED DESCRIPTION OF THE PREFERRED EMBODIMENT

The terms and words used in the following specification are not limited to their literal meanings, but are only used by the present inventor to enable a clear and consistent understanding of the present application. Therefore, the following description of various embodiments of the present application is provided for the purpose of illustration, and not for the purpose of limiting the present application as defined by the appended claims and their equivalents, which are obvious to those skilled in the art.

Although ordinal numbers such as "first," "second," etc. will be used to describe various components, those components are not limited here. The term is only used to distinguish one component from another. For example, the first component can be referred to as the second component, and similarly, the second component can also be referred to as the first component, without departing from the teaching of the present invention. The term "and/or" as used herein includes any and all combinations of one or more of the listed items.

The terms used here are only for the purpose of describing various embodiments and are not intended to limit. As used herein, the singular form is also intended to include the plural form, unless the context clearly indicates otherwise. In addition, the terms "including" and/or "having" when used in this specification specify the presence of the stated features, numbers, steps, operations, components, elements, or combinations thereof, but do not exclude the presence or addition of one or more other features, numbers, steps, operations, components, elements, or combinations thereof.

FIGS. 1 to 8 show a water negative ion air conditioner 1000 according to a preferred embodiment of the present invention. The water negative ion air conditioner 1000 comprises a water negative ion generating device 100 and an air conditioning main body 1001. The water negative ion generating device 100 comprises a water negative ion spraying structure 10, a water storage container 20, a control circuit board 30, and a fan element 40. The water storage container 20 is used to store liquid water, and the water is supplied to the water negative ion spraying structure 10 for the water negative ion spraying structure 10 to generate negative ions by vibrating and having frictional contact with the water. In addition, the water negative ion generating device 100 may also comprises an ionization assembly 50 which is used to supplement the negative ions generated by the water negative ion spraying structure 10 through discharge with negative electrons, so that the negative ions generated by the water negative ion spraying structure 10 tend to be electrically saturated, thereby producing a higher concentration of negative ions.

Figure 1:
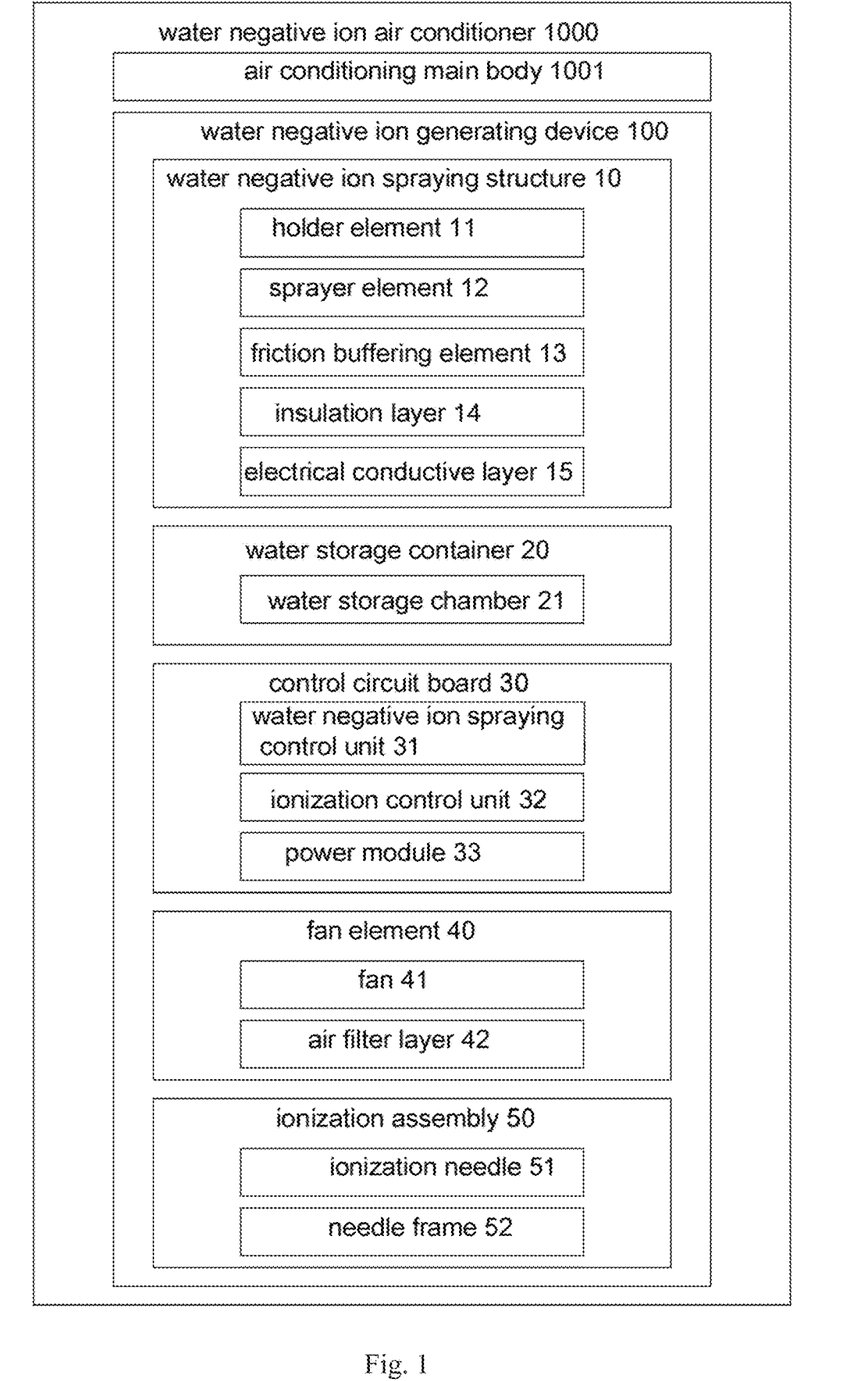
FIG. 1 is a schematic diagram of a water negative ion air conditioner according to a preferred embodiment of the present invention.
Figure 2:
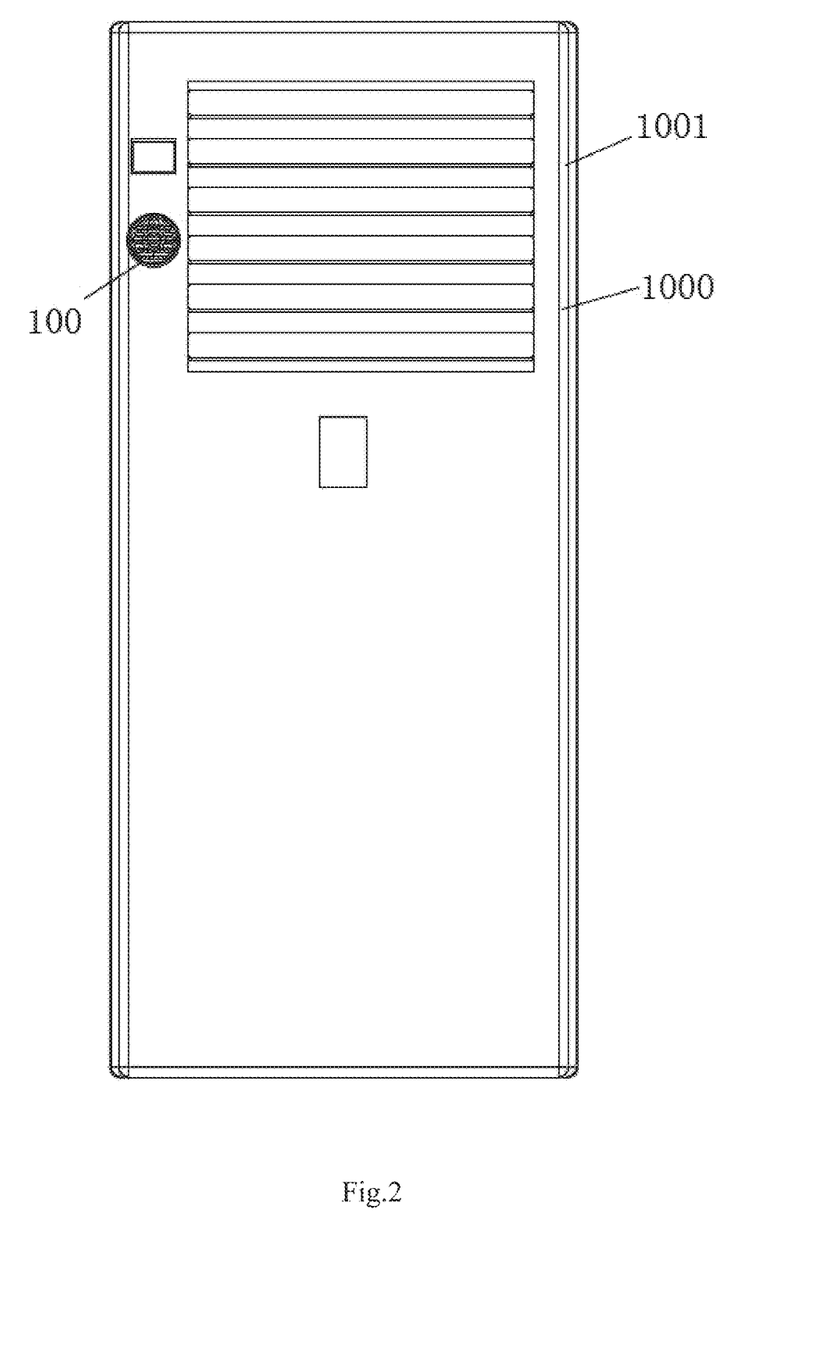
FIG. 2 is a schematic view of the water negative ion air conditioner according to the above mentioned preferred embodiment of the present invention.

The water negative ion generating device 100 is installed on the air conditioning main body 1001 to provide the water negative ion air conditioner 1000 with the function of supplying negative ions. The air conditioning main body 1001 has a common air conditioning structure, which can comprise structures such as a housing, a refrigeration system and/or a warm air system, an air path system, a humidification system, an electrical system, etc., to ensure the normal operation of the air conditioning. It can be understood that the air conditioning main body 1001 can be a central air conditioning, an indoor wall-mounted air conditioning, a vertical air conditioning, a vehicle air conditioning, etc.

It can be understood that the water negative ion generating device 100 can also be used alone to generate water negative ions. Alternatively, it can be installed in other air conditioning devices such as car air conditioners, fresh air systems, etc.

Figure 6:
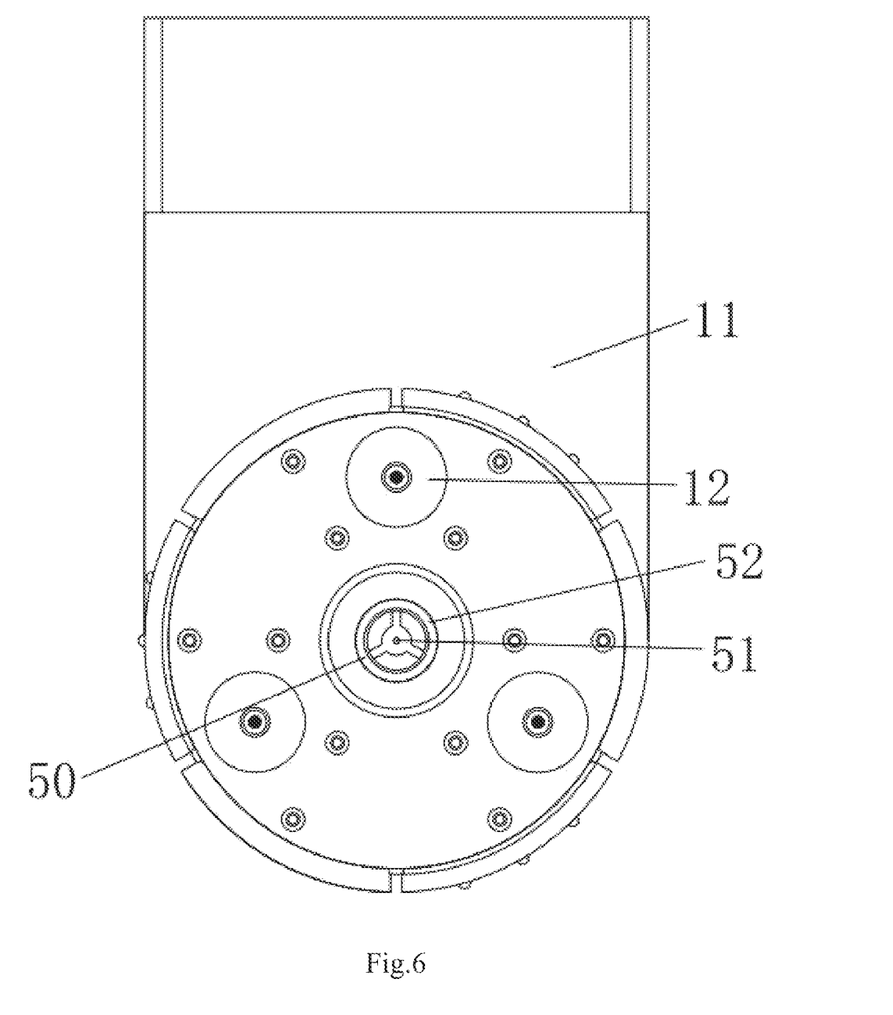
FIG. 6 is a schematic view of a water negative ion spraying structure of the water negative ion generating device according to the above mentioned preferred embodiment of the present invention.
Figure 7:
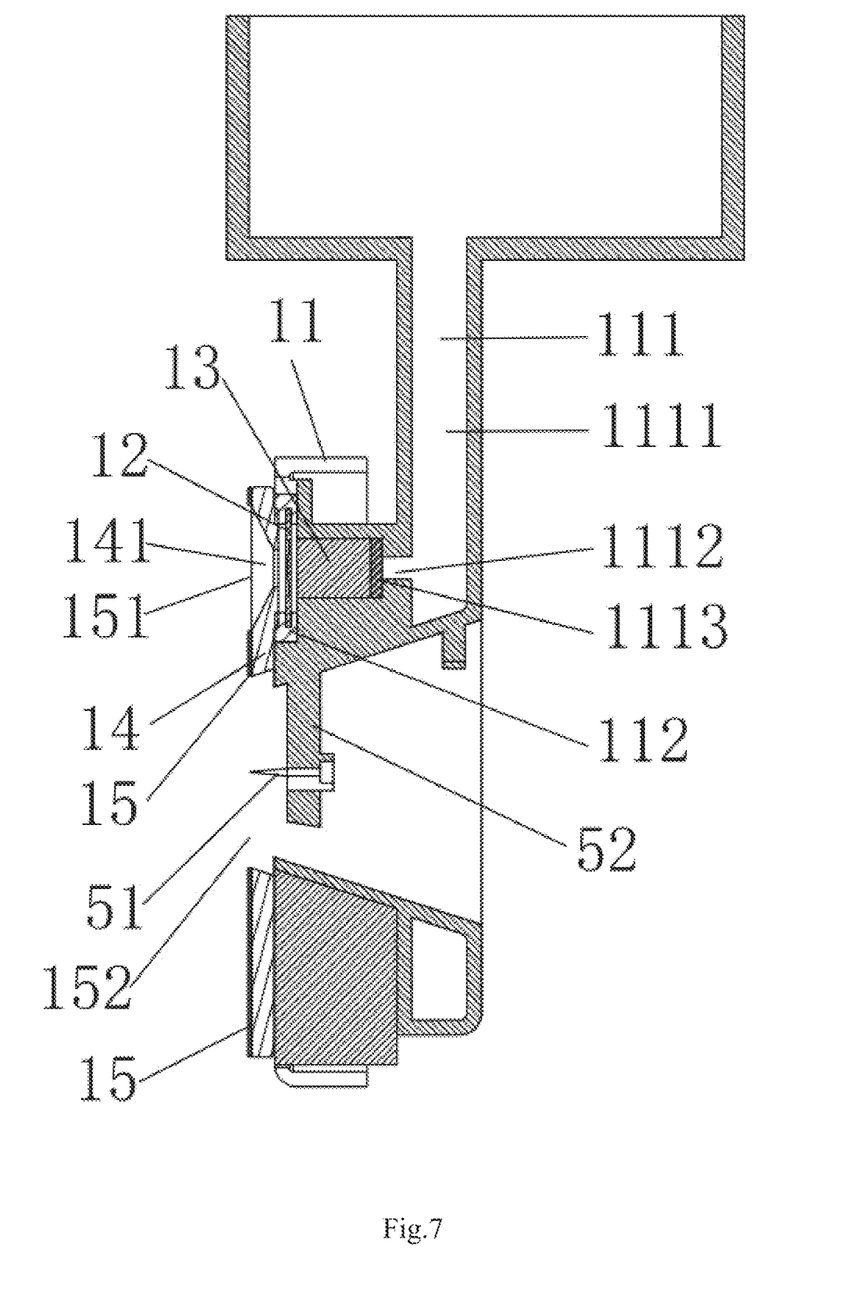
FIG. 7 is a sectional view of the water negative ion spraying structure of the water negative ion generating device according to the above mentioned preferred embodiment of the present invention.

The water negative ion spraying structure 10 comprises a holder element 11, a sprayer element 12, a friction buffer element 13, an insulation layer 14, and an electrical conductive layer 15. The holder element 11 is a supporting carrier for the sprayer element 12, the friction buffer element 13, the insulation layer 14, and the electrical conductive layer 15. The holder element 11 is assembled with the water storage container 20 to guide the water in the water storage container 20 to the friction buffer element 13 and the sprayer element 12, thereby generating negative ions under the action of the sprayer element 12. The water used to generate negative ions can be various suitable types of water, such as drinking purified water, drinking conductive negative ion liquid, and drinking mineral water, etc.

The water storage container 20 has a water storage chamber 21, and the holder element 11 has a connecting channel 111 which is communicated to the water storage chamber 21 of the water storage container 20, so that the water in the water storage chamber 21 can reach the friction buffer element 13 and the sprayer element 12 through the connecting channel 111.

More specifically, the connecting channel 111 comprises a guiding channel 1111, a buffering channel 1112, and a placement channel 1113, wherein the guiding channel 1111, the buffering channel 1112, and the placement channel 1113 are connected in sequence. The guiding channel 1111 is communicated to the water storage chamber 21 of the water storage container 20, and the placement channel 1113 is used to accommodate the friction buffering device 13, and the placement channel 1113 extends laterally from the guiding channel 1111. For example, when the guiding channel 1111 extends in the vertical direction, the placement channel 1113 can extend in the horizontal direction.

Preferably, a buffering channel 1112 is formed between the guiding channel 1111 and the placement channel 1113, and the size of the buffering channel 1112 is smaller than the size of the placement channel 1113, for example, the inner diameter of the buffering channel 1112 is smaller than the inner diameter of the placement channel 1113, so that the friction buffering device 13 can be kept in the placement channel 1113 without entering the buffering channel 1112. The buffering channel 1112 also extends laterally from the guiding channel 1111, for example, its extending direction is in the horizontal direction which is vertically to the guiding channel 1111.

The friction buffer element 13 is made of water absorbent material, so that the friction buffer element 13 accommodated in the placement channel 1113 can absorb water and provide vibration impact water droplets for the sprayer element 12 to generate negative ions. And the friction buffer element 13 can play an elastic buffering role, so that the sprayer element 12, during the process of vibration and friction water, hits on the friction buffer element 13 to obtain buffering and reduce noise. Preferably, the friction buffer element 13 is a cotton swab.

Figure 5:
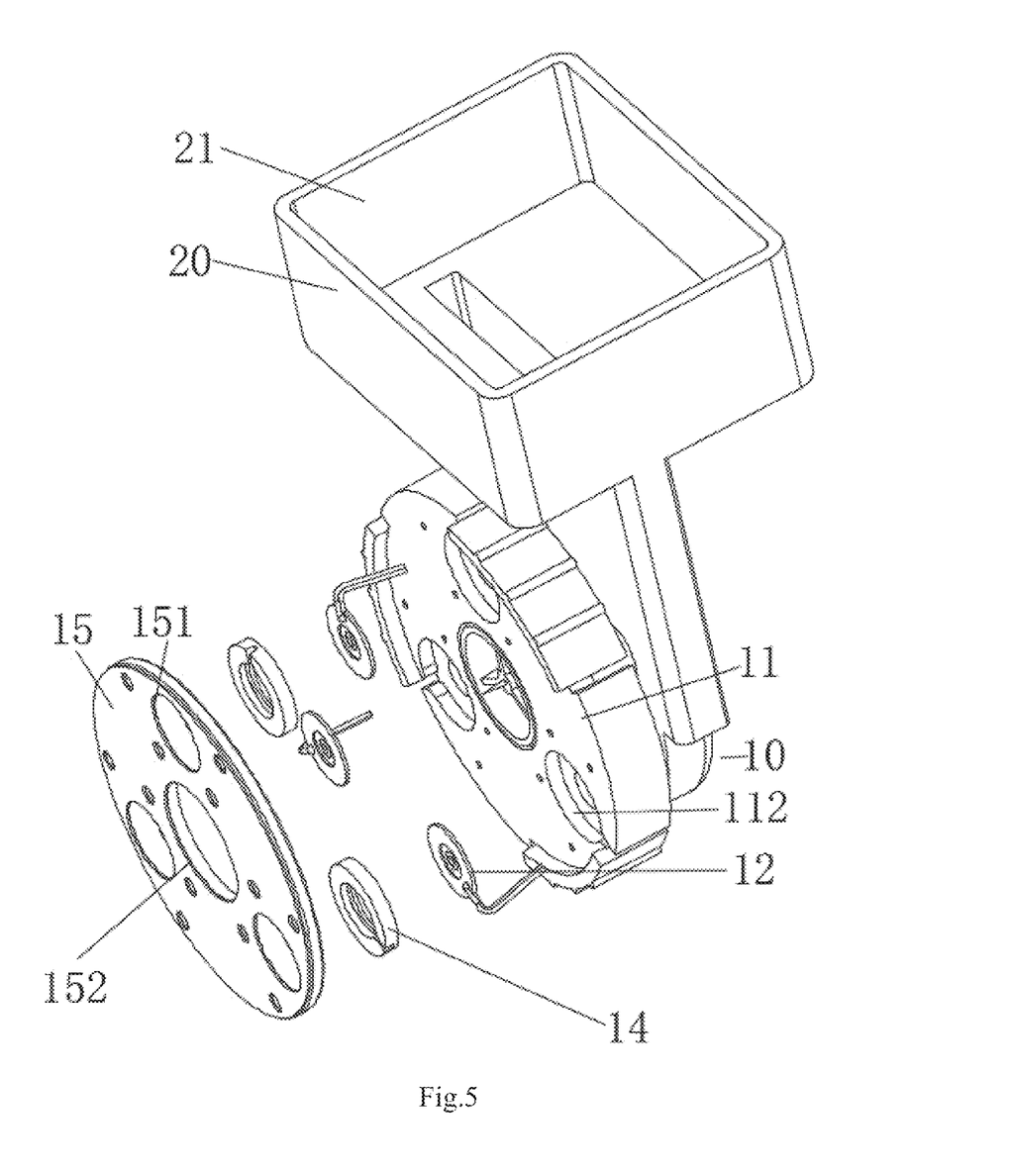
FIG. 5 is a perspective view of the water negative ion generating device of the water negative ion air conditioner according to the above mentioned preferred embodiment of the present invention.

Referring to FIGS. 5 and 7, the water in the water storage chamber 21 of the water storage container 20 flows downward along the vertical direction from the guiding channel 1111 to the buffering channel 1112 extending in the horizontal direction, and then the friction buffer element 13 sucks the water from the buffering channel 1112 into the storage channel 1113, so that the friction buffer element 13 can be a water-absorbed cotton swab for the sprayer element 12 to impact and have frictional contact with the water to generate negative ions.

Figure 8:
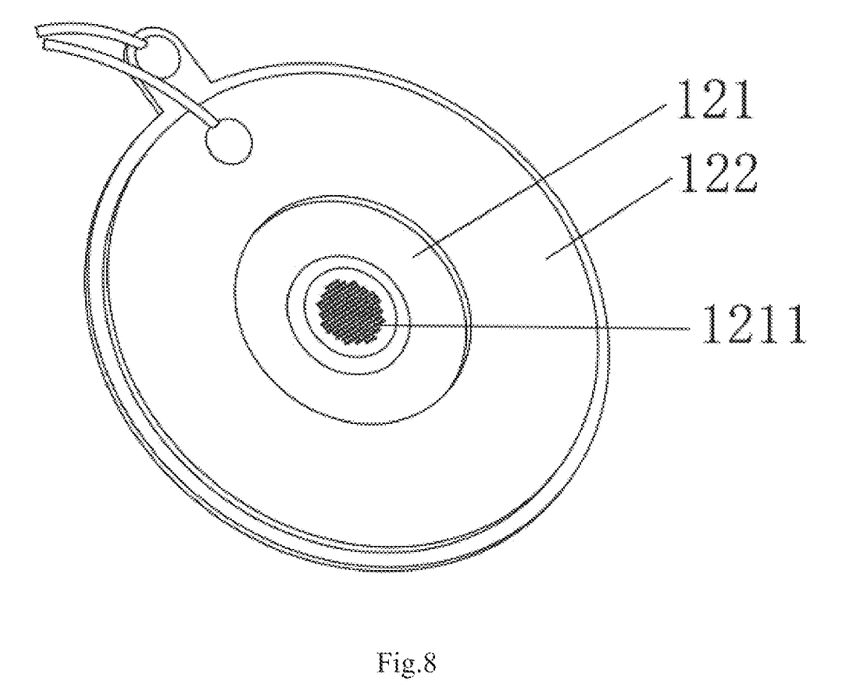
FIG. 8 is a schematic view of a sprayer element of the water negative ion spraying structure according to the above mentioned preferred embodiment of the present invention.

More specifically, as shown in FIG. 8, the sprayer element 12 comprises a spraying piece 121 and a ring-shaped piezoelectric ceramic piece 122 stacked on the spraying piece 121. The spraying piece 121 and the piezoelectric ceramic piece 122 are electrically connected to the control circuit board 30 and are started or stopped under the corresponding driving signal. The spraying piece 121 is made of electrical conductive material and is more prone to losing electrons comparing with water, and a central region thereof has multiple spraying holes 1211. When a voltage with a predetermined frequency and peak value is applied to the spraying piece 121 and the piezoelectric ceramic piece 122, the spraying piece 121 will generate high-frequency vibration to impact the water droplets in the friction buffer element 13, thereby causing the water to resonate and produce tiny water droplets. At the same time, the tiny water droplets will frictionally rub against the spraying piece 121 at a high frequency, further acquiring a negative charge and forming negative ions which then diffuse into the environment through the spraying holes 1211.

In the present invention, in order to generate negative ions, the water negative ion spraying structure 10 is used to perform two processes simultaneously, namely the process of generating small water droplets and the process of making the small water droplets carry negative ions. Specifically, when the spraying piece 121 of the water negative ion spraying structure 10 vibrates at a high frequency, water molecules are driven to resonate at the same frequency and vaporize, thereby generating small water droplets. At the same time, the generated small water droplets rub against and have frictional contact with the vibrating spraying piece 121 at a high frequency, causing the spraying piece 121 to lose its electrons and the small water droplets to acquire the electrons.

It can be understood that in order to make the small water droplets easier to carry the electrons and generate negative ions, the size of the spraying holes 1211 disposed in the spraying piece 121 is made as small as possible and the quantity is increased. In the present invention, the aperture size of the spraying holes 1211 is less than 10 micrometers, preferably with an opening size of less than 5 micrometers. The size of the spraying holes 1211 is correspondingly used to control the size of the small liquid droplets generated by the water negative ion spraying structure 10.

The spraying piece 121 contacts with the water stored in the friction buffer element 13 and is used to excite the production of negative ions. Its material needs to have both conductive friction performance and corrosion resistance. For example, the spraying piece 121 can be a metal alloy such as stainless steel, for example, the spraying piece 121 is made of 316L stainless steel, which is more likely to lose electrons and become positively charged relative to water droplets. To enhance the electrical conductivity, the surface of the spraying piece 121 can also be coated with materials such as polyimide, aluminum, or polyamide such as polyamide (nylon)-11, so that the coating is more likely to lose electrons and carry a positive charge. In this way, when the spraying piece 121 of the water negative ion spraying structure 10 vibrates at a high frequency, the tiny water droplets interact with the coating and are more likely to carry a negative charge, thereby forming negative ions.

The holder element 11 forms a groove 112 at an end of the placement channel 1113 for installing the spraying piece 121 and the piezoelectric ceramic piece 122 of the sprayer element 12. The insulation layer 14 is used to securely install the sprayer element 12 in the groove 112, so that the sprayer element 12 is clamped between the insulation layer 14 and an inner surface of the groove 112.

The insulation layer 14 has a through hole 141 in the middle, which corresponds to the central area of the spraying piece 121 of the sprayer element 12, so that the tiny negative ion water droplets sprayed from the spraying holes 1211 of the spraying piece 121 are sprayed outward from the through hole 141. Both the insulation layer 14 and the holder element 11 are made of insulating material, so that the electrical conductive structure of the sprayer element 12 is sandwiched between the insulation layer 14 and the holder element 11 to avoid short circuit.

The electrical conductive layer 15 is provided on an outer surface of the insulation layer 14 and the holder element 11, and the electrical conductive layer 15 has a discharge channel 151. The position of the discharge channel 151 is aligned with the through hole 141 of the insulation layer 14, so that the tiny negative ion water droplets sprayed from the spraying holes 1211 of the spraying piece 121 can reach the discharge channel 151 of the electrical conductive layer 15 through the through hole 141 and be sprayed outwards from the discharge channel 151. In the present invention, the electrical conductive layer 15 has electrical conductivity, which can prevent charge accumulation on the insulation layer 14. The electrical conductive layer 15 can also be further electrically connected to the control circuit board 30 through a connecting wire for electrostatic discharge treatment, for example, by setting an electrostatic discharge component such as a diode component on the control circuit board 30, the electrical conductive layer 15 can also guide the electrons to the ground through a wire for electrostatic discharge treatment, thereby preventing negative charge accumulation in the water negative ion spraying structure 10. The electrical conductive material of the electrical conductive layer 15 has moisture resistance and electrical corrosion resistance, such as metal or metal alloy, and 314 stainless steel material is preferred in this embodiment.

That is to say, when the sprayer element 12 is in operation, it will cause the accumulation of negative charges, especially if the negative electrons accumulate too much on the insulation layer 14 and the holder element 11 which are made of insulating materials, it is not easy to remove the negative electrons. When the negative charges reach a certain level, a high-voltage electric field is formed and will electrically charging the conductive material in the environment, which may cause the sprayer element 12 to be breakdown and damaged by the electrical charges. If the circuit board in the device is discharged, it will cause irreparable damage.

In addition, the water negative ion generating device 100 of the present invention also comprises an ionization assembly 50 which comprises an ionization needle 51 and a needle frame 52, the ionization needle is installed on the needle frame 52 and electrically connected to the control circuit board 30. The ionization needle 51 is located around the sprayer element 12, and generates negative ions such as negative oxygen ions by ionizing the air. These negative ions are bond to the negative ions generated by the sprayer element 12, so that the negative ions generated by the sprayer element 12 tend to be electrically charged saturated. In this way, the negative ion generating device 100 of the present invention can generate high concentration of negative ions, and the high concentration of negative ions containing elements such as $O_2$-negative molecular group $O_2$—$(H_2O)n$, H+ negative water molecular group $H_3O_2$—$(H_2O)_n$, HO— negative water molecular group OH—$(H_2O)$n, and negative water molecule —$(H_2O)n$.

In other words, the ionization needle 51 will also release negative charges to the surroundings during operation, causing the accumulation of negative electrons, the electrical conductive layer 15 of the present invention can timely export and dissipate the accumulated negative electrons generated during the operation of the sprayer element 12 and the ionization needle 51, thereby preventing the occurrence of electrical discharge phenomena due to high static electricity concentration after a period of use. The electrical conductive layer 15 has an opening 152 in the middle corresponding to the ionization needle 51.

Figure 3:
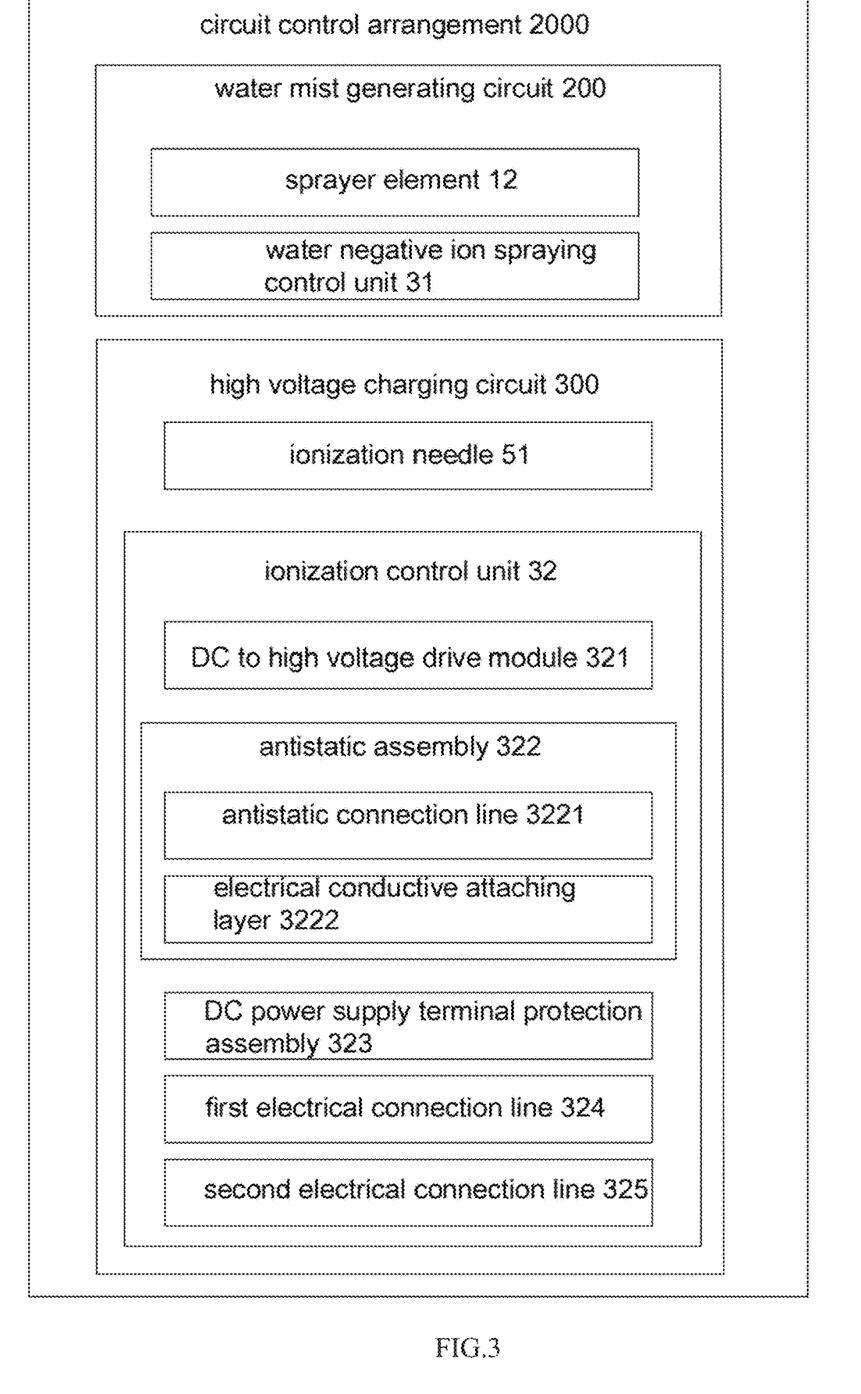
FIG. 3 is a schematic diagram of a circuit control arrangement of a water negative ion generating device of the water negative ion air conditioner according to the above mentioned preferred embodiment of the present invention.

The control circuit board 30 of the present invention comprises a water negative ion spraying control unit 31, an ionization control unit 32, and a power module 33. The water negative ion spraying control unit 31 and the ionization control unit 32 are electrically connected to the power module 33 and can be integrated on one circuit board or separately on individual circuit boards. The water negative ion spraying control unit 31 is used to deliver voltage with a predetermined frequency and peak value to the sprayer element 12, and the ionization control unit 32 is used to deliver voltage to the ionization needle 51.

Referring to FIG. 5 to FIG. 7, the water negative ion spraying structure 10 comprises a circular holder element 11, a plurality of the spraying elements 12, a plurality of friction buffer elements 13, a plurality of insulation layers 14, and an integral circular electrical conductive layer 15. There are a plurality of sprayer elements 12 around the ionization needle 51, so that each ionization needle 51 can provide charge replenishment to the negative ions generated by the plurality of sprayer elements 12 around it during operation.

The water negative ion generating device 100 of the present invention also comprises the fan element 40 which comprises a fan 41 and one or more air filter layers 42. The negative ion generating device can comprises a housing, and the fan 41 and the air filter layers 42 are assembled on the housing. When the fan 41 operates, it sucks air into the housing and filters it through the air filter layers 42 before blowing it towards the water negative ion spraying structure 10 and the ionization assembly 50. In this way, the negative ions generated by the water negative ion spraying structure 10 and the ionization assembly 50 are carried away from the water negative ion generating device 100 by the wind generated by the fan element 40, thereby allowing the negative ions to migrate to a greater distance.

Figure 4:
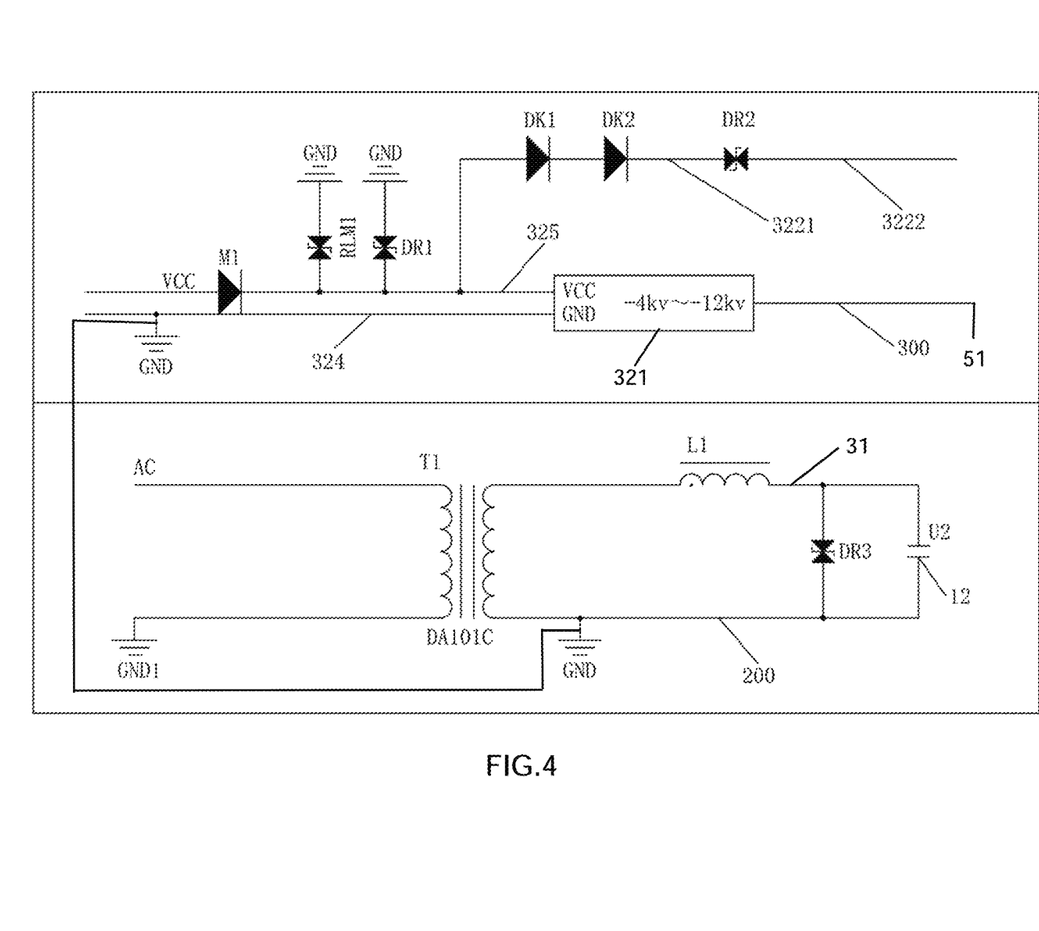
FIG. 4 is a schematic diagram of the circuit composition of the circuit control arrangement of the water negative ion generating device of the water negative ion air conditioner according to the above mentioned preferred embodiment of the present invention.

Referring to FIGS. 3 and 4, the water negative ion generating device 100 of the present invention comprises a circuit control arrangement 2000 which comprises a water mist generating circuit 200 and a high voltage charging circuit 300. The water mist generating circuit 200 comprises the sprayer element 12 and the water negative ion spraying control unit 31, while the high voltage charging circuit 300 comprises the ionization needle 51 and the ionization control unit 32.

The water negative ion spraying control unit 31 comprises a boost transformer T1, power inductor L1, protective component DR3. In the diagram, AC represents the pulse small signal, which is boosted by T1 to the voltage that can drive the water mist generating circuit 200. DR3 is a transient diode (Transient Voltage Suppressor, TVS) which is bidirectional suppression. The main function of DR3 is to prevent the high voltage generated by the high voltage charging circuit 300 from entering the sprayer element 12 through the housing of the water negative ion generating device 100. Once DR3 starts working, it controls the voltage within a safe range and plays a protective role. The reverse cutoff voltage (Vrwm) of DR3 must not exceed a maximum excitation voltage of the sprayer element 12.

The spraying piece 121 and the piezoelectric ceramic piece 122 of the sprayer element 12 are respectively electrically connected to the positive and negative poles of the boost transformer T1, and the protective component DR3 is connected in parallel with the sprayer element 12. After being boosted by the booster T1, the sprayer element 12 is loaded with a voltage of 3K-5 MHZ and a peak value of 60-90V.

The ionization control unit 32 of the high voltage charging circuit 300 comprises a DC to high voltage drive module 321, an antistatic assembly 322, and a DC power supply terminal protection assembly 323. The high voltage charging circuit 300 generates negative electrons through high voltage discharge, and the negative electrons are captured by water molecules to generate negative ion molecules. The antistatic assembly 322 is used to eliminate the electrons attached to the housing of the water negative ion generating device 100 generated during the operation of the high voltage charging circuit 300, and the DC power supply terminal protection assembly 323 is used to protect the power module 33.

The ionization needle 51 is electrically connected to the DC to high voltage drive module 321, and the DC to high voltage drive module 321 increases the voltage to −2 KV or above (such as −2 KV, −3 KV, −4 KV, −5 KV or higher), the preferred voltage is raised to −4 KV or above, generating a negative high voltage with respect to GND. Preferably, the DC to high voltage drive module 321 raises the voltage provided by the power module to −4 KV to −12 KV. The ionization needle 51 can charge the water mist generated by the sprayer element 12, that is, the electrons generated by the ionization needle 51 are promptly absorbed by the water mist generated by the sprayer element 12, thereby generating negatively charged water mist rich in negative ions.

The ionization control unit 32 comprises a first electrical connection line 324 and a second electrical connection line 325. The first electrical connection line 324 is electrically connected to GND (Ground) as a common ground line and serves as a negative pole of the circuit, and the internal ground line is non-isolated. The second electrical connection line 325 is electrically connected to VCC (Voltage Circuit, the power supply voltage), as a positive electrode of the circuit.

In this embodiment, as an example, VCC can be 12V, and the parameters of the DC to high voltage drive module 321 are 10.5±0.5V boost−10 KV±1 KV, with a power less than 3 W.

The antistatic assembly 322 comprises an antistatic connection line 3221 and at least a part of which can be adhered to the housing of the water negative ion generating device 100. The fixing end of the antistatic assembly 322 can be an electrical conductive column such as a copper column which is fixed to the housing. The antistatic assembly 322 also comprises a DR2 and at least one DK2, wherein the DR2 and DK2 are connected in series with the antistatic connection line 3221. In this way, the electrons attached to the housing of the water negative ion generating device 100 are guided to the DR2 and DK2 through the antistatic connection line 3221 to achieve antistatic treatment.

For better static electricity conduction, the antistatic assembly 322 can comprise an electrical conductive attaching layer 3222, such as double-sided conductive aluminum foil or copper foil which can be attached to an inner side of the housing of the water negative ion generating device 100.

In this embodiment, the antistatic assembly 322 can comprise two DKs, such as a DK1 and a DK2 which are series-connected. DK1 and DK2 are both protective components which can be transient diodes, varistors, gas discharge tubes, glass discharge tubes, semiconductor discharge tubes, etc.

In this embodiment, as an example, two DK protection components are embodied as transient diodes each with a bidirectional polarity, the reverse breakdown voltage (Vrwm) is 5.8V, the breakdown voltage (minimum value) is 6.45V, the breakdown voltage (maximum value) is 7.14V, the reverse leakage current (Ir) is 500 uA, the peak pulse current (Ipp) is @10/1000 μs: 58.1 A, and the maximum clamping voltage is 10.5V DO-214AA 600 W VRWM=6.8V.

DK2 selection mainly concerns the designing of the DC reverse withstand voltage (Vr), the DK2 assembly can be achieved by connecting one or more diodes in series, so that the sum of the DC reverse withstand voltages of multiple DK2*s* is greater than the high voltage generated by the DC to high voltage drive module 321. In this embodiment, for example, three diodes can be connected in series, and 3 DK2*s* can be selected to be connected in series together, with a DC reverse withstand voltage of 5 KV, and the sum of the DC reverse withstand voltage of the three connected in series is 15 KV, which is greater than the high voltage of 10 KV±1 KV generated by the DC to high voltage drive module 321.

As an example, in this embodiment, the DC reverse withstand voltage of DK2 is 5 KV, the average rectified current (Io) is 200 mA, the forward voltage drop (Vf) is 5V@200 mA, and the reverse current (Ir) is 5 uA@5 kV.

The DC power supply terminal protection assembly 323, which is arranged on the second electrical connection line 325, comprises one or more diodes M1 and protection components PLM1 and DR1. The diode M1 is connected in series in the second electrical connection line 325, and one end of each of the PLM1 and DR1 is respectively electrically connected to the second electrical connection line 325, and the other end is electrically connected to GND.

M1 can be a general-purpose diode. Its selection mainly depends on the DC reverse voltage (Vr), forward voltage drop (Vf), average rectified current (Io), wherein the main characteristic requirement is that the DC reverse voltage (Vr) is not less than 1 KV. The main function of M1 is to prevent the high voltage charging circuit 300 from generating interference that affects the system power supply VCC.

In this embodiment, as an example, some parameters of M1 model selection are as follows: the diode is configured as an independent type, with a DC reverse voltage (Vr) of 2 KV, an average rectification current (Io) of 1 A, a forward voltage drop (Vf) of 1.1V@1 A, and a reverse current (Ir) of 5 uA@2 kV.

PLM1 is a protective component, such as a transient diode, a varistor, an air discharge tube, a glass discharge tube, a semiconductor discharge tube, etc. DR1 is a transient diode (Transient Voltage Suppressor, TVS) which is bidirectional in polarity.

The protective component of the DC power supply terminal protection assembly 323 comprises at least a DR1. In this embodiment, as an example, the selected parameters of DR1 are reverse breakdown voltage (Vrwm) of 13V, breakdown voltage (minimum value) of 14.4V, peak pulse current (Ipp) of @10/1000 μs: 28, and maximum clamping voltage of 21.5V.

In this embodiment, PLM1 is embodied as the glass discharge tube, with the selection parameters being a DC breakdown voltage of 140V, an accuracy of ±30%, an insulation resistance of 100 MΩ, a static capacitance of 0.8 pF, and a current flow of 300 A for the high-efficiency discharge tube.

Referring to FIG. 4, in order to charge the water droplets generated by the water mist generating circuit 200, a ground GND of the DC to high voltage drive module 321 electrically connected to the ionization needle 51 of the high voltage charging circuit 300 and a ground GND of the water mist generating circuit 200 share a same grounding, that is, the ground GND of the high voltage charging circuit 300 and the ground GND of the water mist generating circuit 200 are directly connected by an electrical connection wire for forming a closed loop for the flow of electrons. Usually, for the high voltage module, from the perspective of electromagnetic compatibility, the power supply and ground inside the high voltage module are isolated from the input power supply and the ground to protect the input voltage and the ground.

It is found in the experiment that when the high voltage charging circuit 300 and the water mist generating circuit 200 are not grounded together, the negative ion generating device 100 with the isolated high voltage module has a significantly smaller amount of negative ions generated, and the presence of negative ions cannot be detected in the basic test at a distance of 6 meters from the water negative ion generating device 100. However, when the high voltage charging circuit 300 and the water mist generating circuit 200 are grounded together, the concentration of negative ions can reach about 30,000/$cm^3$ at a distance of 6 meters from the water negative ion generating device 100.

The above description combines specific embodiments to illustrate the basic principles of the present application. However, it should be noted that the advantages, benefits, and effects mentioned in this application are only examples and not limitations. It should not be assumed that these advantages, benefits, and effects are necessary for all embodiments of the present application. In addition, the specific details disclosed above are provided for illustrative and explanatory purposes only, and should not be considered as limitations. These details do not restrict the implementation of the present application to the specific details disclosed above

What is claimed is:

1. A water negative ion generating device comprising:
a water storage container having a water storage chamber;
a holder element having a placement channel communicated to the water storage chamber;
a friction buffer element made of cotton arranged in the placement channel;
a water mist generating circuit for driving the generation of negative ion water mist, wherein the water mist generating circuit comprises a sprayer element and a water negative ion spraying control unit electrically connected to the sprayer element, wherein the sprayer element comprises a spraying piece with spraying holes and a piezoelectric ceramic piece, so as to vibrate water to generate tiny water droplets through water resonance, at the same time, the tiny water droplets rub against the spraying piece for further acquiring negative electrons and forming negative ions which then diffuse into the environment through the spraying holes, wherein the sprayer element is used to vibrate and rub the water in the friction buffer element; and
a high voltage charging circuit, wherein the high voltage charging circuit comprises an ionization needle and an ionization control unit electrically connected to the ionization needle, wherein the water mist generating circuit and the high voltage charging circuit are grounded together, wherein the ionization control unit comprises a DC to high voltage drive module, wherein the ionization needle is electrically connected to the DC to high voltage drive module for generating electrons, wherein the DC to high voltage drive module increases a voltage of the ionization needle to −2 KV or above, wherein the ionization needle is arranged in a horizontal direction and the sprayer element is located adjacent to the ionization needle and arranged in a vertical direction.

2. The control circuit arrangement according to claim 1, wherein the DC to high voltage drive module increases the voltage to −4 KV~−12 KV.